United States Patent [19]
Quaroni et al.

[11] Patent Number: 5,811,281
[45] Date of Patent: Sep. 22, 1998

[54] IMMORTALIZED INTESTINAL EPITHELIAL CELL LINES

[75] Inventors: Andrea Quaroni; Eileen C. A. Paul, both of Ithaca, N.Y.

[73] Assignee: Cornell Research Foundation, Inc., Ithaca, N.Y.

[21] Appl. No.: 342,434

[22] Filed: Nov. 18, 1994

Related U.S. Application Data

[63] Continuation-in-part of Ser. No. 89,847, Jul. 12, 1993, abandoned.

[51] Int. Cl.$^6$ ............................. C12N 5/10; C12N 15/86
[52] U.S. Cl. ...................................... 435/240.2; 435/320.1
[58] Field of Search ............................... 435/240.2, 320.1

[56] References Cited

PUBLICATIONS

Whitehead et al., *PNAS*, vol. 90, Jan. 1993, pp. 587–591.
Jat et al., *Mol. Cell. Biol.*, vol. 9, 1989, pp. 1672–1681.
Chastre et al., *J. Biol. Chem.*, vol. 266, 1991, pp. 21239–21246.
Wyllie et al., *Cancer Res.*, vol. 52, 1992, pp. 2938–2945.

*Primary Examiner*—James S. Ketter
*Attorney, Agent, or Firm*—Hodgson, Russ, Andrews, Woods & Goodyear

[57] ABSTRACT

Novel intestinal epithelial cell lines having stably incorporated heterologous DNA having a temperature-sensitive mutant oncogene are described, wherein the cell line proliferates at permissive temperatures in a conditionally immortalizing phenotype; and ceases to proliferate at non-permissive temperatures thereby effecting cessation of cell proliferation and a differentiated intestinal epithelial cell phenotype including expression of certain brush border enzymes, and keratin markers.

4 Claims, 5 Drawing Sheets

IMMORTALIZED INTESTINAL EPITHELIAL CELL LINES

This application is a continuation-in-part of U.S. patent application Ser. No. 08/089,847 filed Jul. 12, 1993, now abandoned, which is herein incorporated by reference.

FIELD OF THE INVENTION

The present invention relates to novel cell lines. More particularly, the present invention is directed to the establishment in-vitro of intestinal epithelial cell lines which are immortalized conditionally, and which express a more differentiated intestinal epithelial cell phenotype than the cells from which the cell lines were derived.

BACKGROUND OF THE INVENTION

Intestinal Epithelial Cell Differentiation

Adult small intestinal epithelium is a dynamic system wherein the epithelial cells are renewed continuously by a process involving division of a pluripotent stem cell population located in the crypts, migration of daughter cells along the villus, and extrusion of senescent cells into the lumen. Immature daughter cells undergo proliferation and give rise to progeny which will ultimately yield non-proliferative, terminally differentiated cells which are functionally specialized. Such daughter cells include absorptive enterocytes, goblet cells, enteroendocrine cells, and Paneth cells. Absorptive enterocytes, goblet cells, and enteroendocrine cells are cell types that undergo differentiation/maturation as they migrate up the crypt/ villus wall (Cheng et al., 1974, *Am. J. Anat.* 141:537–561). The cells cease to proliferate and become committed to a particular differentiation pathway in the upper third of the crypts. In absorptive enterocytes, a marked series of distinct morphological, biochemical, and functional changes accompany cell differentiation. In the upper crypt, enterocytes exhibit the ability to secrete chloride (Welsh et al., 1982, *Science* 218:1219–1221), and to transport secretory immunoglobulin (Mostov et al., 1980, *Proc. Natl. Acad. Sci. USA.* 177: 7257–7272). On entering the villus, enterocytes acquire well defined apical microvillar brush border membrane (Grand et al. 1976, *Gastroenterology* 70:790–810); the ability to secrete a number of digestive enzymes including aminopeptidase N (APN), dipeptidyl peptidase IV (DPPIV), lactase, and sucrase isomaltase (Lacroix et al., 1984, *Early Hum. Dev.* 9: 95–103; Lacroix et al., 1984, *Gut.* 25:925–930; Weiser et al., 1973, *J. Biol. Chem.* 248:2536–2541); and the ability to adsorb nutrients ensues. In addition, a marked change of keratins is observed between crypt and villus enterocytes. Enterocytes in the crypt contain keratin 19 as the most abundant, whilst keratin 8 is minor, and keratin 21 is absent. In comparison, keratin isoforms 8 and 21 are predominant in villus enterocytes (Calnek et al., 1992, *Biochem. J.,* 285:939–946).

Applications of Use for Intestinal Epithelial Cells

In the practice of medicine, the enteral (oral) route is the most widely used route of administration of drugs. The advantages of orally administering drugs include the ease, convenience, economy, and effectiveness involved in such administration. However, before a drug can be generally approved for human use, certain information about the drug's properties/abilities is required. Since the small intestine represents the major site of absorption of orally administered drugs, such drugs must be evaluated for their ability to be absorbed by the functionally specialized cells lining the small intestine.

Absorption studies are crucial to determine the amount of drug ("drug levels") which can potentially reach their target of action, and whether the drug is altered or metabolized by interactions with intestinal epithelial cells during the absorptive process. Conventional absorption studies involve administration of a drug to an animal, with the animal serving as an in vivo model, followed by measurements of drug levels in various body fluids as indicia of the drug's ability to be absorbed by the small intestine. Ethical and economical considerations arise with the use of animals as models for absorption studies. Ethically, it would be desirable to reduce or eliminate the use of animals in absorption studies. Economically, absorption studies in animals are also expensive. Additional problems with in vivo studies include the difficulty in controlling the study environment, and the inability to screen a large number of drugs or compounds for their ability to be absorbed. Thus, there is a need for an in vitro model comprising cultured cells which can be used for absorption studies. Desirable characteristics of such cells include a) establishment in a cell line so as to allow continuous passage for growth to large numbers; b) expression of a phenotype, i.e., intestinal epithelial cell differentiation markers, characteristic of the absorptive cells found along the villus wall of the small intestine; and c) absence of chromosomal abnormalities or tumor-associated functions, i.e. malignant characteristics that affect the model's relevance to physiological intestinal function in vivo.

Knowledge Of Intestinal Epithelial Cell Differentiation

The epithelial cells of the small intestine which are predominately involved in an absorptive function are the absorptive villus cells. Typical morphological, biochemical and functional features of absorptive villus cells include a well defined apical microvillar brush border membrane (Dunn, 1967, *J. Anat.* 101:57–68; Grand et al., 1976, supra); a number of digestive enzymes (referred to hereinafter as "brush-border enzymes") including aminopeptidase N (APN), dipeptidyl peptidase IV (DPPIV), lactase, and sucrase isomaltase (Lacroix et al., 1984, supra; Weiser, 1973, supra); and a predominant expression of keratin isoforms 8 and 21 (Calnek et al., 1992, supra).

The mechanisms responsible for regulating intestinal epithelial cell proliferation and the process of differentiation/maturation remain essentially unknown. Intestinal epithelial cells differentiate rapidly from stem cells into mature enterocytes in vivo with a gradient of differentiation along the crypt-villus axis (Darmoul et al., 1991, *Am J Physiol* 261:G763–G769). Further, as exemplified by the brush-border enzyme sucrase-isomaltase, enzyme expression is differentiation dependent and strongly controlled by nutritional and/or metabolic factors, wherein the differentiation dependent expression is primarily controlled by the level of m-RNA (Darmoul et al., 1991, supra). AB summarized in a review of enterocyte division and differentiation (Quaroni, 1990, pages 9–38 in *Malnutrition in Chronic Diet-Associated Infantile Diarrhea* published by Academic Press), expression of brush border enzymes and other differentiated functions during intestinal cell differentiation along the crypt-to-villus axis may be controlled and modulated at several different levels including regulation at the transcriptional, translational, and post-translational levels, and including regulation effected by levels of sugars, and hormones (i.e., glucocorticoids and epidermal growth factor (EGF)). Thus, at the time of the invention it was known by those skilled in the art that not all intestinal epithelial cells will express all differentiation markers that it is genetically capable of doing. Rather, expression of intestinal epithelial differentiation markers appears dependent on such factors as the position in the crypt-villus (proximal to distal) axis (i.e. how far up the intestinal epithelial cells migrate along the intestinal tract); regulation at one or more levels of transcription, translation, or post-translation; and levels of certain nutrients and hormones. Intrinsic factors thought to be involved include peptide growth factors, hormones, and neuropeptides (Buick et al., 1987, *Exp. Cell Res.* 170:300–303; Chastre et al., 1987, *Endocrinology* 121:2211–2221; Cross et al., 1991, *Am. J. Physiol.* 261:C1173–C1183; Weiser et al., 1973, supra). Extrinsic factors thought to be involved include cell-matrix or cell-cell interactions with underlying mesenchyme (Beaulieu, 1992, *J. Cell Sci.* 102:427–436; Kedinger et al., 1987, *Differentiation*, 36:71–85). The precise role of these factors in the control of normal intestinal epithelial cell proliferation and terminal differentiation has not been determined. Thus, the components and conditions required for establishing an optimum environment for in vitro culturing of cells, to differentiate into the phenotype characteristic of absorptive villus cells and for use as an in vitro model for absorption studies, has not been defined.

Current In Vitro Models

Culture of Native Intestinal Epithelial Cells

Efforts to culture native intestinal epithelial cells (i.e., isolated from the small intestine) in-vitro, while still retaining the differentiated phenotypes found in their respective native environment, have not been successful. Freshly dissociated adult villus cells have been cultured in vitro; however, these cells do not remain viable in primary culture for more than two to three hours (See for example, Quaroni, A., pp. 423–428, in *Inflammatory Bowel Disease: current status and future approaches*, ed., R. P. McDermott, Elsevier Science Publishers, 1988). The inability to establish adult villus cells for longer periods in primary culture most likely reflects their intrinsic concerted program of terminal differentiation which leads to cell senescence, rather than inadequate culture parameters. Long term monolayer cultures of intestinal crypt like cells (IEC) have been established from newborn or adult animals. These cultures have proved useful in studying various activities of crypt cells such as regulation of intestinal cell proliferation. However, attempts to induce differentiation of the cells in culture to an absorptive villus cell phenotype have produced unsatisfactory results.

Culture of Transformed Intestinal Epithelial Cells

Another in vitro system used for the study of intestinal cell physiology, cell polarization and regulation of gene expression, involves the use of "transformed" cell lines which are cells derived from human intestinal tumors (Dharmsathaphorn et al., 1984, *Am. J. Physiol.* 246:G204–G208; Pinto et al., 1983, *Biol. Cell.* 47: 323–330; Pinto et al., 1982, *Biol. Cell.* 44: 193–196). These neoplastic cell lines have an incomplete set of enterocyte-like traits (i.e., do not possess the phenotype of differentiation characteristic of absorptive villus cells), and other features including chromosomal abnormalities and tumor-specific functions, which limit their relevance to physiological intestinal functions of absorptive villus cells in vivo. Thus, although the "transformed" cell lines have been useful in certain studies such as expression and intracellular transport of brush border enzymes in polarized cells; ion transport; and electrical properties of enterocytes, the nature of these cells makes them unsuitable for an in vitro model for absorption studies.

Recent attempts to culture rodent and human intestinal epithelial cells have involved the functional insertion of cellular and viral oncogenes, such as c-myc (Pories et al., 1992, *Oncogene* 7:885–893), and SV40 large T antigen (Chastre et al., 1991, *J. Biol. Chem.* 266:21239–21246; Emami et al., 1989, *Proc. Natl. Acad. Sci. USA* 86:3194–3198). Cells derived from such procedures continually proliferate in culture and display very few intestinal differentiation markers. For example, the Emami et al. references discloses an intestinal epithelial cell line having limited differentiation, i.e., villin, enkephalinase, and kertain 8. Since it is well recognized that cells which are highly differentiated are incapable of proliferation, and that cells capable of proliferation display few intestinal differentiation markers, it is likely that these oncogene immortalized cells will never fully differentiate while they maintain the capacity to proliferate.

Human fibroblasts have been transformed with heterologous DNA having a temperature-sensitive mutant oncogene (Jat et al., 1989, *Mol. Cell. Biol.* 9:1672–1681). Primary fibroblast cell lines, containing such a temperature-sensitive mutant oncogene, show growth in culture at permissive temperatures (33° C.), and arrest of growth upon transfer to nonpermissive temperatures (39° C.; hence, the cells are "conditionally immortalized"). However, it was not disclosed whether cells cultured at the nonpermissive temperatures exhibited a more differentiated phenotype then the native cells used in the transformation. Analysis of cellular proteins by gel electrophoresis did not detect differentiation; i.e., when cell extracts prepared from cells grown at permissive temperatures were compared with cells extracts from cells grown at nonpermissive temperatures in analysis by gel electrophoresis, no significant differences in synthesized proteins were detected. Further, even if differentiation in fibroblasts was to be detected in culture, the relevance to intestinal epithelial cells may be questioned. Fibroblast cells are not as fastidious, and are more readily adapted in culture, than intestinal epithelial cells. For example, freshly dissociated fibroblasts cultured in vitro can progress through 30–50 generations before ceasing growth (Jat et al., 1989, supra); whereas freshly dissociated adult villus cells do not remain viable in primary culture for more than two to three hours. Also, as mentioned previously, expression of intestinal epithelial differentiation markers appears dependent on such factors as the position in the crypt-villus (proximal to distal) axis; regulation at one or more levels of transcription, translation, or post-translation; and levels of certain nutrients and hormones.

Therefore, there exists a need for an in vitro system of intestinal epithelial cells as a model for drug transport/absorption in the small intestine.

SUMMARY AND OBJECTS OF THE INVENTION

The present invention is directed to the establishment of immortal intestinal epithelial cell lines which are capable of proliferation, and can be induced to display a phenotype of differentiation markers characteristic of absorptive villus cells.

Thus, one object of the present invention is to establish intestinal epithelial cells in culture, with the capacity to survive and/or grow for extended periods of time in vitro.

Another object of the present invention is to immortalize conditionally intestinal epithelial cells with an oncogene which can be used to control the cells' proliferation process.

Another object is to provide culture conditions and/or components for in vitro culture of conditionally immortalized intestinal epithelial cells which induce the cells to display a phenotype of differentiation markers characteristic of absorptive villus cells.

A further object of the present invention is to identify and characterize the proliferation and differentiation characteristics of conditionally immortalized epithelial cells.

BRIEF DESCRIPTION OF THE FIGURES

In the accompanying drawings,

FIG. 4A represents Northern blot analysis of total RNA with radio-labeled cDNA probe for keratin 8 (24 hour exposure to film). Lane 1 contains RNA from fetal rat intestine (4 µg). Lane 2 contains RNA from 2/4/Al cells cultured at 32° C. Lane 3 contains RNA from 2/4/Al cells cultured at 39° C.

FIG. 4B represents Northern blot analysis of total RNA with radio-labeled cDNA probe for keratin 19 (24 hour exposure to film). Lane 1 contains RNA from fetal rat intestine (4 µg). Lane 2 contains RNA from 2/4/Al cells cultured at 32° C. Lane 3 contains RNA from 2/4/Al cells cultured at 39° C.

FIG. 4C represents Northern blot analysis of total RNA with radio-labeled cDNA probe for keratin 21 (36 hour exposure to film). Lane 1 contains RNA from fetal rat intestine (4 µg). Lane 2 contains RNA from 2/4/Al cells cultured at 32° C. Lane 3 contains RNA from 2/4/Al cells cultured at 39° C.

FIG. 4D represents Northern blot analysis of total RNA with radio-labeled cDNA probe for actin (4 hour exposure to film). Lane 1 contains RNA from fetal rat intestine (4 µg). Lane 2 contains RNA from 2/4/Al cells cultured at 32° C. Lane 3 contains RNA from 2/4/Al cells cultured at 39° C.

DETAILED DESCRIPTION OF THE INVENTION

Figure 1:
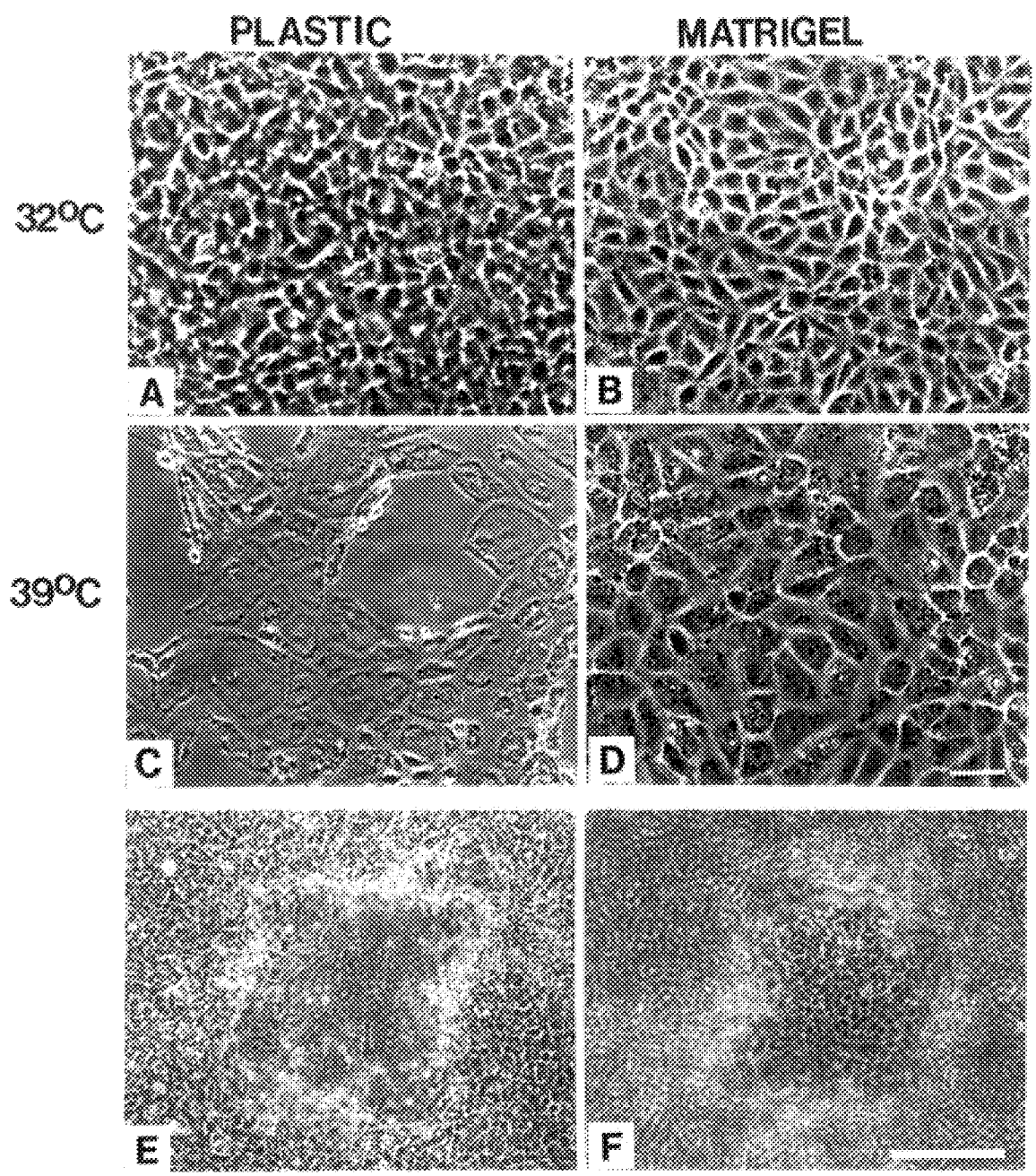
FIG. 1A represents phase-contrast morphology of 2/4/Al cells (passage 20) grown on plastic at 32° C.
FIG. 1B represents phase-contrast morphology of 2/4/Al cells (passage 20) grown on a extracellular matrix component preparation (diluted 1:3) at 32° C.
FIG. 1C represents phase-contrast morphology of 2/4/Al cells (passage 20) grown on plastic at 39° C.
FIG. 1D represents phase-contrast morphology of 2/4/Al cells (passage 20) grown on an extracellular matrix component preparation (diluted 1:3) at 39° C.
FIGS. 1E & F represent phase-contrast morphology showing dome formation of 2/4/Al cells cultured at 32° C. on plastic.

The cell lines of the present invention comprise mammalian intestinal epithelial cells which are immortalized conditionally with a temperature-sensitive mutant oncogene used to control proliferation of the cell lines. The cell lines of the present invention have stably incorporated into their genome a temperature-sensitive mutant of an oncogene thereby allowing a mechanism to regulate the expression of that oncogene. In one embodiment of the present invention, the temperature-sensitive mutant of an oncogene used to conditionally immortalize cells was a thermolabile simian virus 40 (SV40) large T antigen (SVtsa58) under the control of the SV40 early promoter. It is important to be able to regulate the expression of large T antigen since transformation of cells often results in de-differentiation. As noted above, transformation of cells with a "normal" large T antigen results in cell lines which exhibit continued proliferation, and few differentiation markers (See for example, Chastre et al., supra; and Emami et al., supra). Further, the inventors have tried using an oncogene (SV40 large T antigen) under the control of an inducible promoter, such as the heavy metal inducible mouse metallothionein-I (MT-I), to conditionally immortalize mammalian intestinal epithelial cells. However, resultant cell lines produced sufficient T antigen to allow them to proliferate both when the MT-I promoter was induced and uninduced, suggesting that the T antigen gene under these conditions is constitutively expressed in intestinal epithelial cells (Paul et al., 1993, *Am. J. Physiol.* 265:C266–C278).

Since the oncogene used in the present invention is a temperature-sensitive mutant, cells grown at 32° C. ("permissive temperature) contain functional T antigen which acts to initiate and maintain the cells in a transformed state thereby allowing them to proliferate continuously in culture. However, growing the cells at 39° C. ("nonpermissive temperature") results in the suppression of large T antigen function thereby causing the cells to cease to proliferate. Thus, the term "conditionally immortalized" refers to cells transfected with heterologous DNA having a temperature-sensitive mutant of an oncogene, wherein the oncogene is incorporated into their genome, and wherein the resultant cell lines proliferate in culture at permissive temperatures but cease to proliferate at nonpermissive temperatures.

Other cellular and viral oncogenes, having the ability to establish continuous proliferation in primary cells, for which a temperature-sensitive mutant thereof may be useful to conditionally immortalize intestinal epithelial cells, as illustrated by the present invention, include myc, fos, p53; and adenovirus E1a, polyomavirus large T-antigen, and the papillomavirus E7, respectively. At permissive temperatures, the level of temperature-sensitive mutant oncogene expressed may be readily detectable in the conditionally immortalized cells, such as by SDS-PAGE with Western blot analysis. Upon a shift to nonpermissive temperatures, functional temperature-sensitive mutant oncogene is not detected, as the thermolabile mutant oncogene is either inactivated or rapidly degraded after incubation at the higher temperatures (nonpermissive temperature).

As summarized above, typical morphological, biochemical and functional features of absorptive villus cells include a well defined apical microvillar brush border membrane; expression of brush-border enzymes aminopeptidase N (APN), dipeptidyl peptidase IV (DPPIV), lactase, and sucrase isomaltase; and a predominant expression of keratin isoforms 8 and 21. It was discovered that intestinal epithelial cell line of the present invention, in addition to displaying arrested growth upon culture in vitro at nonpermissive temperature, also displayed a phenotype of differentiation markers characteristic of absorptive villus cells. More particularly, and when cultured on a surface having extracellular matrix components, the intestinal epithelial cell line was maintained for periods of greater than 18 days, and expressed at least the differentiated intestinal epithelial cell phenotype of expression of brush border enzymes sucrase isomaltase and lactase and aminopeptidase N and dipeptidyl peptidase IV, and of expression of keratin markers keratin 8 and keratin 21. Thus, the presence of extracellular matrix components enhances adhesion of the intestinal epithelial cell line of the present invention, and thereby provides the effects that adhesion has on the differentiation process. Therefore, inclusion of extracellular matrix components, when culturing the cell line of the present invention, is preferred because of the maintenance and differentiation characteristics required for use as an in vitro model for absorption studies.

The term "extracellular matrix components" is defined herein as a preparation containing as the major ingredients, a combination of basement membrane proteins. Examples of extracellular matrix components that may be used to enhance cell maintenance and differentiation of the intestinal epithelial cell line of the present invention include: collagen in various combinations with one or more of laminin, entactin (nidogen), fibronectin, and heparin sulfate; human placental extracellular matrix; and basement membranes prepared from tumor cells. In a preferred embodiment, the extracellular matrix components is a preparation extracted from the Englebreth-Holm-Swarm (EHS) mouse sarcoma, having as its major ingredients laminin, collagen IV, heparin sulfate proteoglycans, and entactin. A commercially available source of the preferred extracellular matrix components, which also contains growth factors, is MATRIGEL™.

EXAMPLE—MATERIALS AND METHODS
Primary Intestinal Cell Culture And Transfection:

Fetal rat intestines at 16–18 days of gestation served as a source for mammalian intestinal epithelial cells. A population of epithelial cells was isolated from the intestine by dissociation with ethylenediamino tetra-acetate (EDTA). Cells were cultured in Dulbecco's modified Eagle's Medium (DME) containing 4.5 g/l glucose supplemented with 10 mM HEPES pH 6.5, 2 mM glutamine, 50 U/ml penicillin, 50 µg/ml streptomycin & 10% fetal bovine serum (FBS) at 37° C. in 6% $CO_2$. Contaminating non-epithelial cells (mostly fibroblasts) attach faster to the plastic culture dishes than epithelial cells. Therefore, the fibroblasts can be removed by a one hour pre-incubation followed by transfer of the supernatant containing most of the epithelial cell clusters in suspension to new culture dishes.

Cells which adhered to the plastic culture vessel after 18 hours of incubation were then transfected heterologous DNA containing a temperature-sensitive mutant oncogene, wherein the oncogene is selected from the group consisting of adenovirus E1a, SV40 large T antigen, polyomavirus large T antigen, papillomavirus E7, myc, fos, and p53. Cells were transfected using the lipofection method according to the instructions of the manufacturer (GIBCO-BRL). Other methods of delivering the vector DNA into the target cells are known in the art and may be substituted for lipofection. These alternate methods include electroporation, viral infection, and transfection such as by $CaPO_4$ precipitation. pZipSVtsa58 transfected cells were cultured in DME & 10% FBS at 32° C. in 6% $CO_2$. Two days after lipofection, the cells were placed under G418 sulphate (200 µg/ml) selection. After 6 to 8 weeks, the number of colonies surviving the drug selection were isolated using standard trypsinization procedures and cloning cylinders. Cell lines were maintained in DME & 10% FBS and cultured on plastic tissue culture dishes or dishes coated with extracellular matrix components (MATRIGEL™, diluted at 1:3 (v/v) with DME); 50 µl/cm² were applied to the dishes and allowed to adhere during a 30 minute incubation at 37° C.

Antibodies

Monoclonal antibodies to native brush border enzymes (Quaroni et al., 1979, *J. Cell Biol.* 80:248–265; Quaroni, A., 1988, in *Inflammatory Bowel Disease*, supra; and Quaroni et al., 1985, *Dev. Biol.* 111:267–279); to rat cytokeratins (Quaroni et al., 1991, *J. Biol. Chem.* 266:11923–11931); to the tight junction-associated protein ZO-1 (rat monoclonal antibody MAB1250, Calbiochem); and to the SV40 large antigen (Gurney et al., 1980, *J. Virology* 34: 752–763) have been previously described. The antibodies DRBB2/33 and DRBB2/158 to denatured rat lactase and sucrase-isomaltase, respectively, were prepared by fusion of NSI mouse myeloma cells with spleen cells obtained from BALB-c mice immunized with affinity purified antigens, denatured with SDS, as previously described for the corresponding human antigens (Quaroni et al., 1992, *Int. J. Cancer* 51:404–411). Each mouse received one primary subcutaneous immunization consisting of antigens mixed with complete Freund's adjuvant, and three i.p. booster injections (with incomplete Freund's adjuvant) at monthly intervals. With each injection, each mouse received the amount of antigens present in 2 mg of purified brush border membranes. Hybridoma cells were selected and screened by immunoblotting, using purified brush border membrane proteins separated by SDS-PAGE and transferred to nitrocellulose membranes, as target antigens. The DRBB2/33 and DRBB2/158 hybridomas were cloned twice by dilution plating and used for antibody characterization and large-scale antibody production in ascites form. The antibodies produced by these hybridomas are of the $IgG_1$ class. The antigen specificity was determined by immunoblotting of affinity purified brush border enzymes (lactase, sucrase, maltase, aminopeptidase, dipeptidyl peptidase IV (DPPIV), alkaline phosphatase) as previously described (Quaroni, A., 1988, in *Inflammatory Bowel Disease,* supra). Only sucrase-isomaltase was stained with DRBB2/158, whereas only lactase was stained with DRBB2/33. Both antibodies recognize the corresponding antigens only when the antigen is denatured.

Immunofluorescence

Formaldehyde and methanol/acetone fixed cells were stained by an indirect immunofluorescence technique previously described (Quaroni et al., 1985, supra). Staining for actin was achieved using rhodamine-conjugated phalloidin. After antibody incubations and washings, the cells were mounted in glycerol:PBS (9:1)+2.5% 1,4-diazabicyclo-[2.2.2]-octane (DABCO) and coverslips added. Cells were examined with a fluorescence microscope and the fluorescent images were saved to an optical disk and subsequently transferred to film.

Protein immunoprecipitation and Western blot analysis

Total cell membrane fractions of the transformed cells were solubilized, and immunoprecipitated with antibodies bound to beads (AFFIGEL-10™ beads). Immunoprecipitated antigens were eluted from the antibody-beads conjugates and subjected either to 10% or 6.5% SDS-PAGE under reducing conditions (50 mM DTT). Proteins were transferred to nitrocellulose and immunoblotted.

Brush border membrane enzyme assays

Total cell membrane fractions were solublized, and immunoprecipitated with antibodies bound to the beads. The immunoprecipitates were assayed for the presence of lactase, sucrase, isomaltase, aminopeptidase N, and DPPIV as previously described (Quaroni, A., 1985, *J. Cell. Biol.* 100:1611–1622).

Purification and Analysis of RNAs by Northern Blotting

Total RNA was extracted from cells and the integrity of the RNA was verified by ethidium bromide staining and the quantity was determined spectrophotometrically. Conditions used for Northern blotting, including the stringencies of post-hybridization washes, have been described previously (Calnek et al., 1992, supra). Prehybridization was performed in a solution consisting of 5× Denhardts solution, 5× SSC (750 mM NaCl, 75 mM sodium citrate pH 7), 0.1% sodium-pyrophosphate, 8 mM EDTA, 0.5% SDS and 100 μg/ml denatured salmon sperm DNA at 65° C. for 2 hours. Hybridization was carried out in the above solution with the addition of $^{32}$P-randomly prime labeled heat-denatured keratin 8 CDNA insert (859 base pairs (bp)), keratin 19 cDNA insert (440 bp), keratin 21 insert (800 bp) or Drosophila actin cDNA insert (1700 bp) at 65° C. for 15 hours. After the post-hybridization washes, filters were kept moist and exposed to x-ray film with two intensifying screens at −70° C. After a suitable exposure period, the keratin and actin probes were removed from the blots and a bovine 18S rRNA probe was hybridized to the filters and then removed by stringent washing in 1×SSC, 0.1% SDS at 65° C. RNA was quantitated using a densitometer; the amounts of keratin and actin RNA were standardized to the 18S rRNA.

$^3$H-Thymidine Uptake and Autoradiography

Cells growing on 35-mm dishes were labelled with 2 μCi of [$^3$H]thymidine (20 Ci/mmol) per ml complete DME for 2 hours or 24 hours. Cells were rinsed twice in PBS and fixed twice in cold 5% TCA (trichloroacetic acid) for 10 minutes. Cells radiolabelled for 2 hours were processed for liquid scintillation counting by solubilizing the cellular material in 0.1 NaOH. An aliquot of the solubilized material was removed for protein determination while the remainder was neutralized by the addition of acetic acid, and then liquid scintillation fluid was added. Cells radiolabelled for the 24 hour period were coated in KODAK NTB™ Nuclear track emulsion, exposed in the dark for 5 days at 4° C., and developed and counterstained with Giemsa. Each sample was performed in triplicate.

EXAMPLE—CONDITIONALLY IMMORTALIZED INTESTINAL EPITHELIAL CELLS

This embodiment is in accordance with the procedures and methods described in the preceding Example. To illustrate the establishment of intestinal epithelial cells with a temperature-sensitive mutant of an oncogene, primary cultures of fetal rat intestinal cells (18 days gestation) were transfected with pZipSVtsa58 (obtained from Dr. V. Cherrington of Tufts University, and described in Jat et al., supra). The salient features of this plasmid are that it contains the SV40 heat labile T-antigen under the control of the wild-type SV40 early region promoter; and a gene which confers resistance to G418 sulphate useful for the selection of transfected cells. A minimum of 40 colonies were observed and removed from the culture dish using cloning cylinders and expanded. All of the clones stained positive for T antigen when cultured at 32° C., while no staining for T antigen was visible after incubating the cells at 39° C. for 2–3 days. Four of the cell lines obtained, designated 2/4/Al; 2/3/A7; 3/2/A9; and 3/3/A9 stained positive for keratin 8, indicating their epithelial origin, and were selected for further analysis.

Cell Morphology and Adherent Properties

Light microscopic examination of the conditionally immortalized intestinal epithelial cells showed a different morphology when cultured at 32° C. versus 39° C. For example, cell lines 2/4/Al (FIG. 1) and 2/3/A7 (not shown) were seen to round up and float into the culture medium during day 2 and 3 of culture in the nonpermissive temperature (FIG. 1C) when cultured without the addition of extracellular matrix components. This observation that these cells become less adherent as they cease to proliferate fits well with what is observed for normal intestinal cells undergoing terminal differentiation through their passage in the villus and eventual exfoliation into the intestinal lumen (Cheng et al., 1974, supra). However, some cells remained attached to the plastic culture dish even after 7 days of growth at the nonpermissive temperature. These cells tended to flatten out onto the unoccupied plastic substrate and adopted a more "epithelial" morphology becoming less spindle shaped and more polygonal. By contrast, cell lines 3/2/A9 and 3/3/A9 could not be maintained for more than 3 days when the temperature was shifted to nonpermissive temperature (39° C.). 2/4/A1 cells grown on plastic at permissive temperatures (32° C.) showed some piling up. However, when these cells were cultured on a surface with extracellular matrix components (MATRIGEL™) at 32° C., they exhibited a tight, cobblestone appearance (FIG. 1B). Growth of this cell line on MATRIGEL™ enabled the cells to be maintained at 39° C. for periods of more than 18 days while maintaining a tight epithelial morphology (FIG. 1D). On both plastic and MATRIGEL™, cells cultured at 39° C. (FIGS. 1C & 1D) were typically larger than those cultured at 32° C. (FIGS. 1A & 1B). Mitotic cells were not visible after incubating the cells for 2 days at the nonpermissive temperature. Dome formation was observed on cells cultured at permissive temperatures (FIGS. 1A & 1F) but not at nonpermissive temperatures.

Cell Proliferation

Cell line 2/4/A1 was assessed for proliferative capacity at 32° C. versus at 39° C. Cells were incubated at 32° C. or 39° C. for 24 hours, 48 hours, 72 hours, 96 hours, and 120 hours. During these times the cells were either pulse labelled with $^3$H-thymidine for two hours and then prepared for scintillation counting and protein determination, or radiolabelled for 24 hours and then prepared for autoradiography. The combined results obtained from autoradiography (not shown) and the $^3$H-thymidine pulse labelling data (Table 1) indicate that the cells ceased to proliferate between 48 and 72 hours of incubation at 39° C., i.e. no nuclear staining was observed after incubating the cells at 39° C. for 72 hours and the level of $^3$H-thymidine incorporation into DNA was basal ($2.6 \times 10^3$ cpm/mg represents 8.5% of the label that is incorporated at 32° C. and probably represents thymidine that is required for DNA repair and maintenance). Thus, cell line 2/4/A1 ceases to proliferate between 48 and 72 hours of incubation at 39° C.

TABLE 1

Incorporation of [$^3$H] thymidine into cellular DNA in 2/4/A1 cells cultured at 32° C. or 39° C.

| Hours of incubation | Temperature (°C.) | cpm/mg* |
| --- | --- | --- |
| 24 | 32 | $3.5 \times 10^4 \pm 8.8 \times 10^2$ |
| 24 | 39 | $6.1 \times 10^3 \pm 3.1 \times 10^2$ |
| 48 | 32 | $2.1 \times 10^4 \pm 6.3 \times 10^2$ |
| 48 | 39 | $2.2 \times 10^3 \pm 9.9 \times 10^1$ |
| 72 | 32 | $1.5 \times 10^4 \pm 5.3 \times 10^2$ |
| 72 | 39 | $2.6 \times 10^3 \pm 1.5 \times 10^2$ |
| 96 | 32 | $6.7 \times 10^3 \pm 2.4 \times 10^2$ |
| 96 | 39 | $3.3 \times 10^3 \pm 1.9 \times 10^2$ |
| 120 | 32 | $4.8 \times 10^3 \pm 2.5 \times 10^2$ |
| 120 | 39 | $3.0 \times 10^3 \pm 9.6 \times 10^1$ |

*cpm of incorporated radioactivity per mg cellular protein, average of three determinations ± SEM Expression of Mutant Oncogene and Intestinal Differentiation The immortalized intestinal cell lines were analyzed for the expression at 32° C. and 39° C. of the SV40 large T antigen and intestinal differentiation markers. The cells lines, in the presence of G418 sulphate, were grown at the permissive (32° C.) temperature and also at the nonpermissive (39° C.) temperature for 3–5 days. Cells were examined by immunofluorescence for the presence of SV40 T antigen; keratins 8, 19, and 21; and the brush border enzymes sucrase isomaltase, lactase, aminopeptidase N (APN), and DPPIV.

Mutant Oncogene Expression

Figure 2:
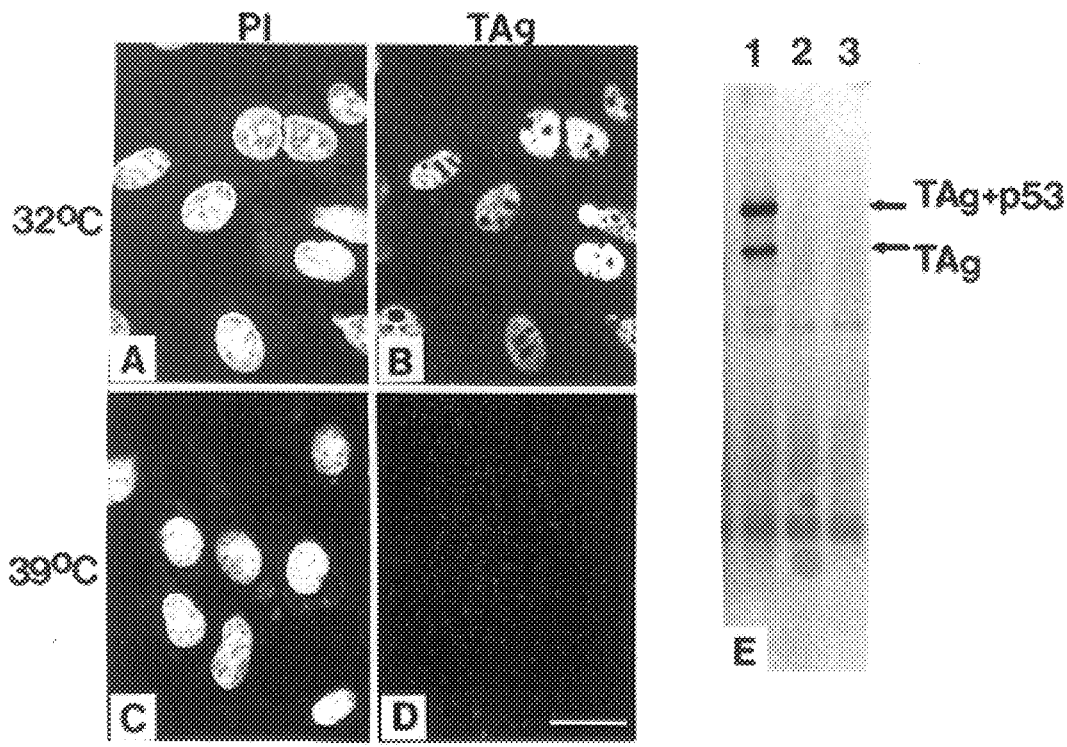
FIG. 2A represents immunofluorescent staining with propidium iodide (PI) of 2/4/Al cells cultured at 32° C.
FIG. 2B represents immunofluorescent staining for SV40 T antigen (TAg) of 2/4/Al cells cultured at 32° C.
FIG. 2C represents immunofluorescent staining with propidium iodide (PI) of 2/4/Al cells cultured at 39° C.
FIG. 2D represents immunofluorescent staining for SV40 T antigen (TAg) of 2/4/Al cells cultured at 39° C.
FIG. 2E represents Western blot analysis for the detection of SV40 T antigen (TAg) from cells cultured for 3 days, and immunoprecipitated with anti-T antigen bound to AFFIGEL-10™ beads. The immunoprecipitates were subjected to sodium dodecyl sulfate polyacrylamide gel electrophoresis (SDS-PAGE) and Western blotted with anti-T antigen antibody. Lane 1 contains protein from 2/4/Al cells cultured at 32° C. Lane 2 contains protein from 2/4/Al cells cultured at 37° C. Lane 3 contains protein from 2/4/Al cells cultured at 39° C.

Results revealed that the immortalized cells expressed SV40 antigen at the permissive temperature (FIG. 2B). However, no T antigen was discernable when the immortalized cells were grown at the nonpermissive temperature (FIG. 2D). Western blot analysis was performed on protein preparations from cells grown at the permissive temperature and nonpermissive temperature. SV40 T antigen (MWt 92 Kd) was readily detectable in cells incubated at 32° C. (FIG. 2E, lane 1). T antigen was not detected after 72 hours of incubation at 37° C. (FIG. 2E, lane 2), nor was it detectable at 39° C. (FIG. 2E, lane 3). The higher molecular weight species detected on the Western blot (FIG. 2E, lane 1) is most likely the product of the interaction between the tumor suppressor p53 and SV40 T antigen (Levine et al., 1991, Virology, 351:453–456).

Keratin Isoform Expression

Figure 3:
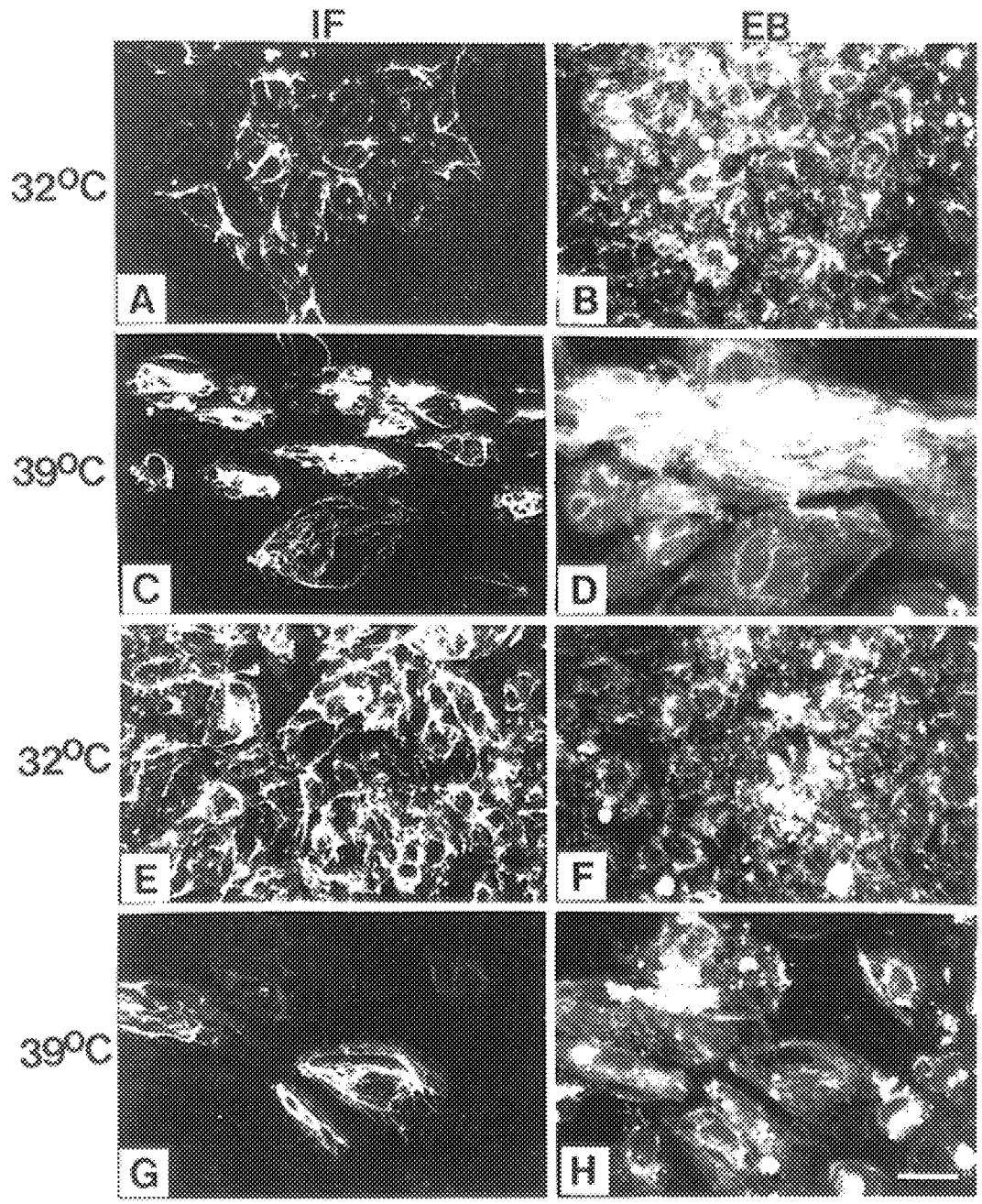
FIG. 3A represents immunofluorescence (IF) staining of 2/4/Al cells cultured at 32° C. using a monoclonal antibody to keratin 8.
FIG. 3B represents counterstaining with Evans blue (EB) of 2/4/Al cells cultured at 32° C.
FIG. 3C represents immunofluorescence (IF) staining of 2/4/Al cells cultured at 39° C. using a monoclonal antibody to keratin 8.
FIG. 3D represents immunofluorescence (IF) staining of 2/4/Al cells cultured at 32° C. using a monoclonal antibody to keratin 19.
FIG. 3E represents counterstaining with Evans blue (EB) of 2/4/Al cells cultured at 32° C.
FIG. 3F represents immunofluorescence (IF) staining of 2/4/Al cells cultured at 39° C. using a monoclonal antibody to keratin 19.
FIG. 3G represents counterstaining with Evans blue (EB) of 2/4/Al cells cultured at 39° C.
FIG. 3H represents counterstaining with Evans blue (EB) of 2/4/Al cells cultured at 39° C.

Four cell clones (designated 2/4/A1; 2/3/A7; 3/2/A9; and 3/3/A9) were diagnosed as being positive for certain markers of intestinal epithelial cells: keratins 8 and 19, APN, and DPPIV. The pattern of keratin 8 expression in cell line 2/4/A1 was impressive in that less than 5% of the cells incubated at 32° C. had a scant array of keratin filaments (FIG. 3A). However, after culturing these cells at 39° C. for 3–4 days, over 90% of the cells in the population displayed a rich architecture of keratin filaments (FIG. 3C). In contrast, all of the 2/4/A1 cells stained positive for keratin 19 when cultured at 32° C. (FIG. 3D) but significantly fewer were stained for keratin 19 at 39° C. (FIG. 3F). Keratin 21 staining was not discernable.

Figures 4, 6:
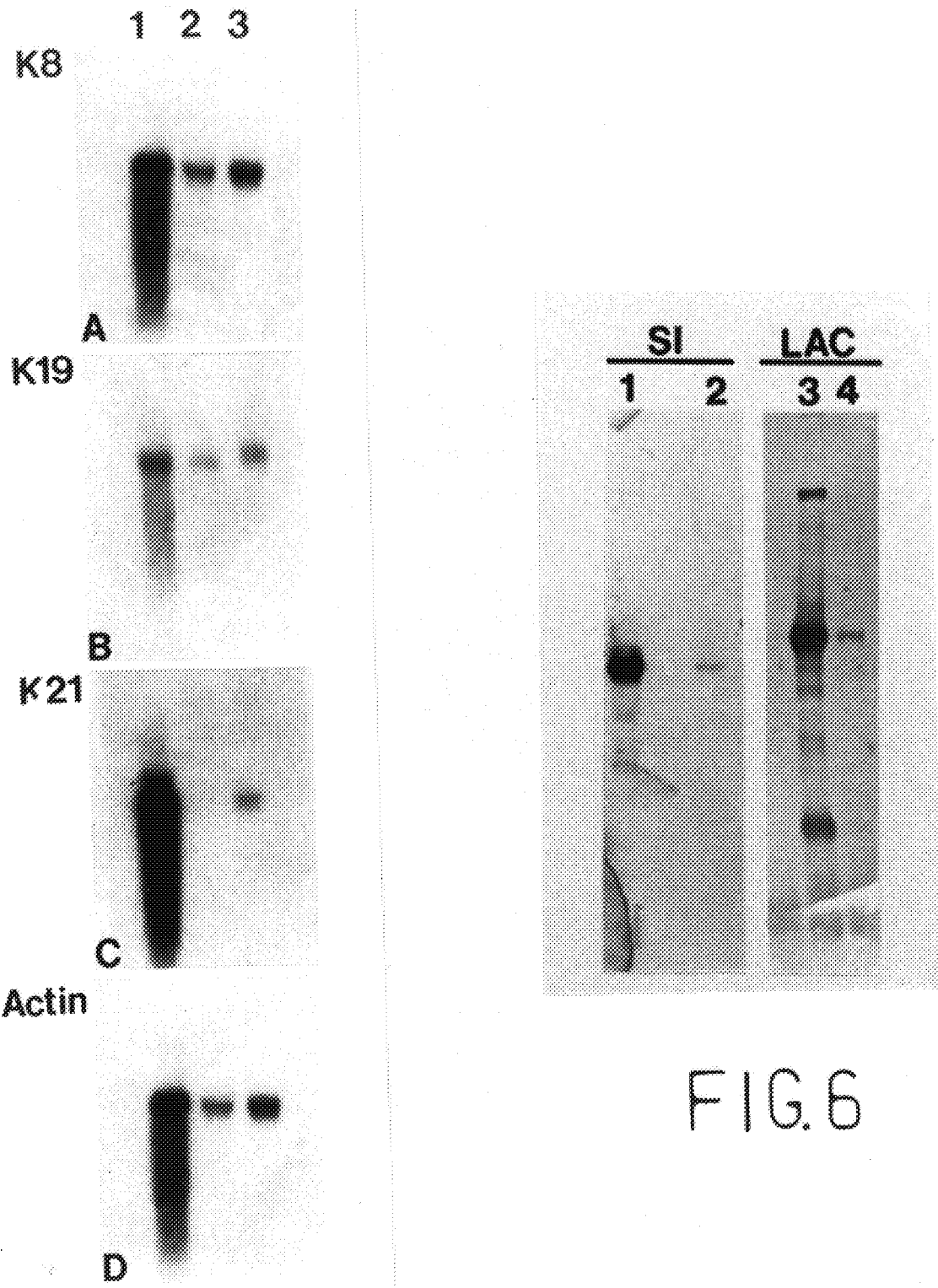
FIG. 6 represents immunoblotting analysis for the brush border enzymes sucrase isomaltase, and lactase. Lane 1 contains protein immunoprecipitated from rat brush border membranes. Lane 2 contains protein immunoprecipitated from 2/4/Al cells cultured at 32° C. Lanes 1 and 2 were incubated with antibody DRBB2/158 specific for denatured sucrase isomaltase. Lane 3 contains protein immunoprecipitated from rat brush border membranes. Lane 4 contains protein immunoprecipitated from 2/4/Al cells cultured at 32° C. Lanes 3 and 4 were incubated with antibody DRBB2/33 specific for denatured lactase.

Keratin isoform expression was also analyzed by Northern blot analysis. Northern blot analysis of RNA transcripts specific for each of these keratins indicated that there was a four-fold increase in the level of keratin 8 transcripts in cells cultured at 39° C. (FIG. 4A, lane 3) versus 32° C. (FIG. 4A, lane 2). Keratin 19 message remained almost unchanged during the switch from proliferative to non-proliferative growth phase (FIG. 4B, lanes 2 & 3). Additionally, an increase in size of the keratin 19 transcript was observed in cells cultured at 39° C. Keratin 21 transcripts were not detected in 2/4/A1 cells cultured at 32° C. FIG. 4C, lane 2), but were present in cells cultured at 39° C. (FIG. 4C, lane 3). Thus, transcription of the keratin 8 gene and the keratin 21 gene in 2/4/A1 was induced by a switch to the nonpermissive temperature, induction of both keratin genes being consistent with normal intestinal cell differentiation from native crypt cells to differentiated enterocytes.

Brush Border Enzyme Expression/Activity

The immortalized intestinal epithelial cell lines were assayed for brush border enzyme activity. Cell lines 2/4/A1, 2/3/A7, 3/2/A9, and 3/3/A9 were maintained at 32° C. for 5 days until they reached confluency. Once confluency was attained, some of the cells continued to be maintained at 32° C., while other cells of the population were incubated at 37° C. or 39° C. for a further 3 days. Total cell membranes were harvested from the cells, and the presence of specific brush border enzymes were assayed after immunoprecipitation (results shown in Table 2). The enzyme activity was standardized to total cell protein in the homogenates. Positive controls of rat brush border membranes (BBM) and negative controls (no membranes) were also included.

Figure 5:
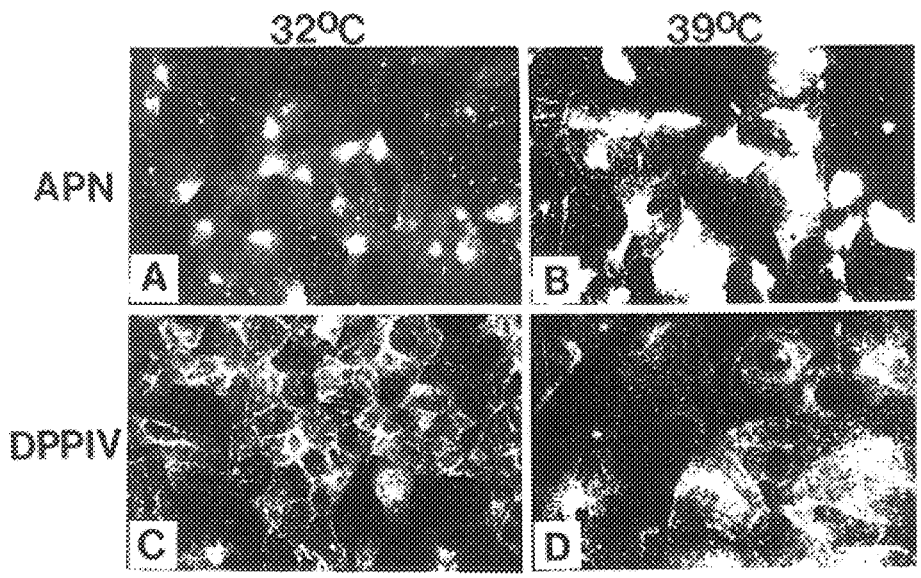
FIG. 5A represents immunofluorescence staining with a monoclonal antibody to aminopeptidase N (APN) of 2/4/Al cells grown at 32° C.
FIG. 5B represents immunofluorescence staining with a monoclonal antibody to aminopeptidase N (APN) of 2/4/Al cells grown at 39° C.
FIG. 5C represents immunofluorescence staining with a monoclonal antibody to dipeptidyl peptidase IV (DPPIV) of 2/4/Al cells grown at 32° C.
FIG. 5D represents immunofluorescence staining with a monoclonal antibody to dipeptidyl peptidase IV (DPPIV) of 2/4/Al cells grown at 39° C.

In the cell line 2/4/A1, the level of APN activity increased approximately 11.5 fold, and DPPIV activity increased approximately 4 fold, during the switch from the proliferative to the non-proliferative growth phase. This increase can be partially attributed to an increase in expression of these enzymes at the apical surface of the cells as evidenced by an increase in immunofluorescence staining for APN and DPPIV at the nonpermissive temperature. At 32° C., a weak staining pattern was observed for APN at the apical surface of the cells (FIG. 5A). However, immunofluorescence staining of cells that were incubated at 39° C. resulted in a strong, vivid, heterogenous staining appearance over their apical surface (FIG. 5B). Similarly, staining of DPPIV was weak in cells cultured at 32° C. (FIG. 5C) but strong in cells cultured at 39° C. (FIG. 5D). Thus, the increase in APN and DPPIV levels exhibited in cell line 2/4/Al after the switch to non-permissive temperature was corroborated by the immunofluorescence pattern showing a marked increase in both these proteins at the nonpermissive temperature. An increase in DPPIV and APN is consistent with the differentiation of mammalian crypt cells to villus cells (Darmoul et al., 1991, Am J. Physiol. 261: G763–G769; Noren et al., 1989, FEBS Letters 259:107–112). The other cell lines produced more variable results, as indicated in Table 2. The enzymes lactase, maltase, and sucrase isomaltase were also assayed, but they were below the limits of detection with the amounts commonly used in the respective assays.

TABLE 2

APN and DPPIV enzyme activities in homogenates of immortalized intestinal cell lines

| Cell line | Temperature (°C.) | APN (mU/g)* | DPPIV (mU/g)* |
|---|---|---|---|
| 2/4/A1 | 32 | 28.3 ± 2.0 | 8.2 ± 1.4 |
| 2/4/A1 | 37 | 63.4 ± 5.2 | 23.2 ± 6.9 |
| 2/4/A1 | 39 | 326.0 ± 17.2 | 33.6 ± 5.2 |
| 2/3/A7 | 32 | 91.6 ± 12.4 | 37.8 ± 3.7 |
| 2/3/A7 | 37 | ND** | 32.7 ± 3.4 |
| 2/3/A7 | 39 | ND | 67.2 ± 7.9 |
| 3/2/A9 | 32 | 88.3 ± 12.2 | 20.1 ± 3.2 |
| 3/2/A9 | 37 | 195.3 ± 15.1 | 63.2 ± 9.5 |
| 3/2/A9 | 39 | 336.5 ± 19.6 | 154.3 ± 12.9 |
| 3/3/A9 | 32 | 217.5 ± 18.4 | 88.0 ± 16.2 |
| 3/3/A9 | 37 | 332.7 ± 24.2 | 134.5 ± 14.7 |
| 3/3/A9 | 39 | 362.9 ± 27.2 | 75.9 ± 7.6 |

*Enzyme activities expressed as mU per g of protein, and as the average of three determinations ± SEM
**ND — nondetectable As illustrated in Table 2, these four conditionally immortalized cell lines analyzed did not display identical phenotypes. Variables that could account for such differences include the number of copies of the oncogene and the region where the oncogene incorporated into the genome; as well as the stage of differentiation of the transfected cells.

Conditionally immortalized intestinal cell line 2/4/Al was analyzed for the presence of specific brush border enzymes by immunoprecipitation and Western blot analysis. Total membranes were prepared from cell line 2/4/Al after culturing the cells at 32° C. and 39° C. Antibodies specific for lactase (BBC1/35), sucrase isomaltase (YBB2/61), and maltase were bound to AFFIGEL-10™ beads and incubated with total membrane proteins. After sufficient incubation, the immunoprecipitated proteins were eluted from the antibodies and subjected to SDS-PAGE and Western blotting. Results revealed that trace amounts of sucrase isomaltase (FIG. 6, lane 2), and lactase (FIG. 6, lane 4) could be detected in 2/4/Al at both temperatures, while maltase was not detectable (not shown).

Cell Structures

Conditionally immortalized intestinal cell line 2/4/Al was analyzed for the presence of ZO-1, a peripheral membrane protein associated with tight junctions. This protein was detected by immunofluorescence staining in 2/4/Al cells cultured at 39° C. (FIG. 7C), but not at 32° C. (not shown). This result is puzzling since domes formed at 32° C., indicative of the presence of functional tight junctions. Also, these structures were observed by electron microscopy. Representative transepithelial electrical resistance measurements of 57 ohms/cm$^2$, obtained from 2/4/Al cells grown at 32° C., were also indicative of the presence of functional tight junctions, as well as of transporting epithelial monolayers. Thus, 2/4/Al displays differentiated cell structures phenotypically characteristic of normal differentiated intestinal cells: The upper surface of the 2/4/Al monolayer was covered with microvilli, and the asymmetry of the cells, and the presence of tight junctions, suggest that the monolayer was polarized. These phenotypes are displayed in native enterocytes (Levine et al., 1991, supra).

Figure 7:
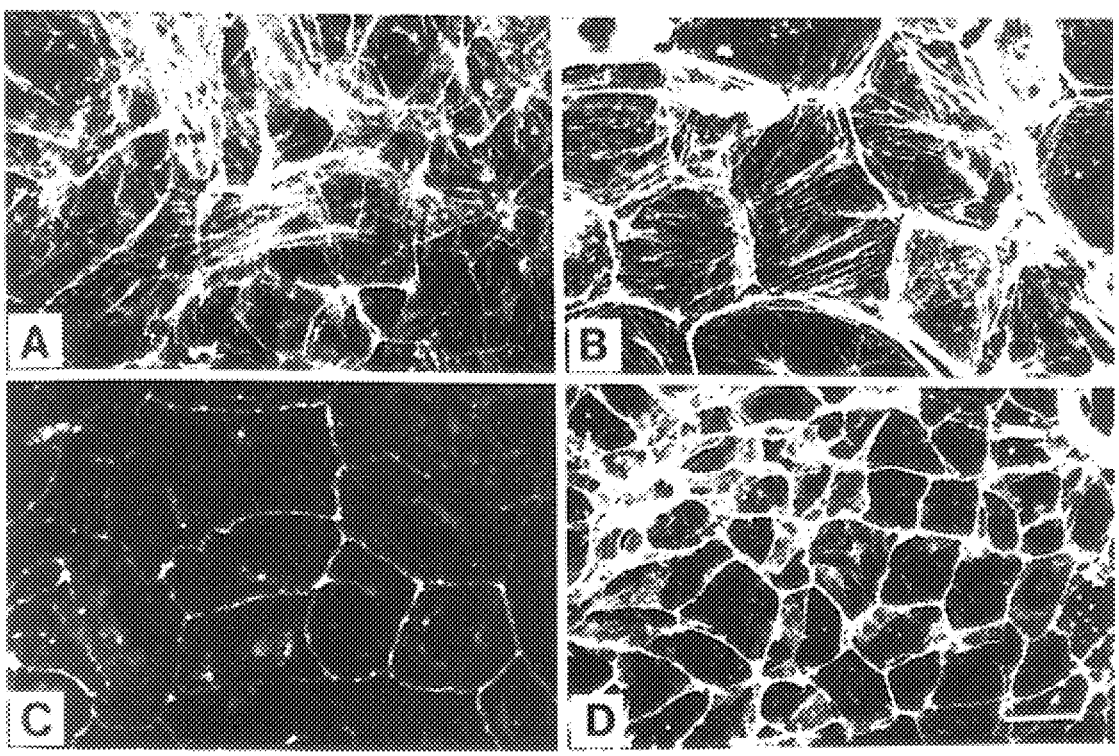
FIG. 7A represents immunofluorescence staining of actin with rhodamine phalloidin of 2/4/Al cells cultured at 32° C. on plastic.
FIG. 7B represents immunofluorescence staining of actin with rhodamine phalloidin of 2/4/Al cells cultured at 32° C. on an extracellular matrix component preparation (diluted 1:3).
FIG. 7C represents immunofluorescence staining of tight junction associated protein ZO-1 with antibody MAB1250 of 2/4/Al cells cultured at 39° C. on plastic.
FIG. 7D represents immunofluorescence staining of actin with rhodamine phalloidin of 2/4/Al cells cultured at 39° C. on an extracellular matrix component preparation (diluted 1:3).

A perijunctional ring pattern of staining of actin microfilaments is characteristic of cells expressing tight junctions, and typically inserts into the lateral membrane of epithelial cells (Madara et al., 1981, Dev. Biol. 86:170–178). This staining pattern was observed for 2/4/Al cells cultured at both 32° C. (FIG. 7B) and 39° C. (FIG. 7D) on diluted MATRIGEL™ with medium supplemented with 2.5% serum. In addition, a large number of stress fibers were observed in cells cultured at 39° C. (FIG. 7B). In FIG. 7A, a more random array of actin filaments with stress fibers is visible in cells cultured at 32° C. on plastic (at this serum concentration, cells do not adhere to the plastic when cultured at 39° C.). The level of actin transcripts increased approximately 1.5 fold on transfer to the nonpermissive growth temperature (FIG. 4D).

Discussion

Typical morphological, biochemical and functional features of absorptive villus cells include a well defined apical microvillar brush border membrane; expression of brush-border enzymes aminopeptidase N (APN), dipeptidyl peptidase IV (DPPIV), lactase, and sucrase isomaltase; and a predominant expression of keratin isoforms 8 and 21. It was discovered that intestinal epithelial cell line of the present invention, in addition to displaying arrested growth upon culture in vitro at nonpermissive temperature, also displayed differentiation markers characteristic of absorptive villus cells that is defined herein as "at least the differentiated intestinal epithelial cell phenotype of expression of brush border enzymes sucrase isomaltase and lactase and aminopeptidase N and dipeptidyl peptidase IV, and of expression of keratin markers keratin 8 and keratin 21 and peripheral membrane protein ZO-1". The phrase "at least the differentiated intestinal epithelial cell phenotype of expression of brush border enzymes sucrase isomaltase and lactase and aminopeptidase N and dipeptidyl peptidase IV, and of expression of keratin markers keratin 8 and keratin 21 and peripheral membrane protein ZO-1", as used in the description of the present invention, refers to the following characteristics of the intestinal epithelial cell lines observed after being cultured in vitro at a nonpermissive temperature for about three days or more after a shift from a permissive temperature to a nonpermissive temperature:

a) cessation of cell proliferation;

b) as observed by immunofluorescence, at least about a 10 fold increase in the number of cells expressing keratin 8 as compared to cells cultured at the permissive temperature;

c) expression of keratin 21;

d) an increase in expression of brush border enzymes at the apical surface of the cells including (i) at least about a 4 fold to 12 fold increase in the level of APN activity, (ii) at least about a 2 fold to 5 fold increase in DPPIV activity, as compared to the cells cultured at the permissive temperature;

e) expression of sucrase isomaltase and lactase;

f) expression of peripheral membrane protein ZO-1; and g) at least about a 1.5 fold increase in the expression of actin, as compared to the cells cultured at the permissive temperature.

Deposit of Cell Line

As a best mode known to the inventor at the time of filing of the application, conditionally immortalized intestinal epithelial cell line 2/4/Al has been deposited with the American Type Culture Collection, Rockville, Md., on Jul. 8, 1993, and was assigned ATCC Designation CRL 11396.

EXAMPLE—USE OF OTHER TEMPERATURE-SENSITIVE MUTANT ONCOGENES

A limited number of the known viral and cellular oncogenes have the ability to immortalize, i.e. establish the continuous proliferation in culture of, primary cells. The viral oncogenes known to immortalize cells include adenovirus Ela, SV40 large T antigen, polyomavirus large T antigen, and papillomavirus E7. The cellular oncogenes include myc, fos, and p53. Using techniques known in the art, temperature-sensitive mutants of these oncogenes can be constructed by those skilled in the art. For instance, temperature-sensitive mutants of SV40 (Jat et al., 1989, supra) and of polyoma large T antigen (Rassoulzadegan et al., 1983, *Proc. Natl. Acad. Sci USA*, 80:4354–4358) have been described previously. In accordance with the procedures and methods described in Example 1, and as illustrated in Example 2, a temperature-sensitive mutant of an oncogene of the above-identified subgroup of oncogenes known to immortalize cells, may be introduced into less differentiated mammalian intestinal cells resulting in conditionally immortalized intestinal epithelial cells that can be induced to exhibit a wide range of intestinal epithelial differentiation markers.

EXAMPLE—CONDITIONALLY IMMORTALIZED INTESTINAL EPITHELIAL CELLS AS IN IN VITRO MODEL

In accordance with the procedures and methods described in Example 1, and as illustrated in Example 2, conditionally immortalized intestinal epithelial cells can be induced to express a wide range of intestinal epithelial differentiation markers characteristic of absorptive villus cells including at least the differentiated intestinal epithelial cell phenotype of expression of brush border enzymes sucrase isomaltase and lactase and aminopeptidase N and dipeptidyl peptidase IV, and of expression of keratin markers keratin 8 and keratin 21 and peripheral membrane protein ZO-1; as well as induction of a change in adhesive properties characteristic of differentiation. Because the conditionally immortalized intestinal epithelial cells, when cultured at nonpermissive temperatures, display differentiation markers and cell morphology characteristic of absorptive villus cells, the conditionally immortalized intestinal epithelial cells may be used as an in vitro model regarding the development and differentiation of normal intestinal epithelium; for drug transport or absorption studies; and drug metabolism studies using standard techniques known in the art for testing drugs in cultured cells.

Drug Absorption and Metabolism Studies

For purposes of illustration, an in vitro model for drug absorption studies may incorporate use of conditionally immortalized intestinal epithelial cells, according to the present invention, in the following embodiment. Conditionally immortalized intestinal epithelial cells are made and cultured according to the materials and methods described in the preceding Examples. The conditionally immortalized cells are cultured in standard flasks at permissive temperature to provide and maintain a large stock of cells. From the stock of cells, cells are seeded onto permeable supports, such as polycarbonate filter cell culture chamber inserts, at a high seeding density which depends on the size of the support used and the time period desired before confluency is reached. The permeable support may be coated with extracellular matrix components to improve adhesion of the cells once transferred to nonpermissive temperature, and for enhancement of differentiation characteristics that may be induced by improved adhesion. After seeding, the cells are incubated on the permeable supports at permissive temperature for a short period until confluency is reached. The cells are then shifted to nonpermissive temperature and incubated for a period of 3 days or longer to allow for a differentiation.

The chamber in which the in vitro absorption studies is performed, typically consists of a donor chamber and acceptor chamber, both containing a physiological solution, which are separated by the permeable support containing the differentiated cells. The physiological solution may be adjusted to a pH of from 6.0 to 7.5 to mimic the pH conditions of the small intestine. The drug to be tested is added to the physiologic solution contained within the donor compartment, wherein the permeable support is placed such that the conditionally immortalized intestinal epithelial cells are in contact with the solution in the donor compartment, in measuring absorption in the lumenal to serosal direction. The cells may also be preequilibrated with the drug prior to the absorption study. By knowing the starting concentration of the drug, at one or more desired time points, drug levels from the donor and acceptor compartments can be determined to ascertain any loss due to absorption to the cell surface, intracellular accumulation, absorption to the permeable support, and/or intracellular degradation or metabolism. Similarly, the permeable support may be removed, and the permeable support and/or cells may be analyzed for absorbed drug.

Many variations of this illustration will become apparent to those skilled in the art using this in vitro model and the cells according to the present invention. Such variations include, but are not limited to, testing of compounds other than "drugs", and the addition of co-factors to monitor the effect of the presence of co-factors in drug or compound absorption by the cells. The term "drug" may include therapeutic or prophylactic compounds that are administered orally and include, but are not limited to, the following classes of compounds: analgesics, antacids, anti-microbials, antihistamines, anti-inflammatories, antineoplastics, antipyretics, nutrition supplements, hormones, immunosuppressives, psychotropics, peptides, and vaccines.

It should be understood that while the invention has been described in detail herein, the examples were for illustrative purposes only. Other modifications of the embodiments of the present invention that are obvious to those of ordinary skill in the art of molecular biology, developmental cell biology, pharmacology, and related disciplines are intended to be within the scope of the appended claims.

What is claimed is:

1. An intestinal epithelial cell line cultured in vitro which consists of conditionally immortalized intestinal epithelial cells containing heterologous DNA comprising a temperature-sensitive mutant oncogene, wherein the oncogene is selected from the group consisting of adenovirus Ela, SV40 large T antigen, polyomavirus large T antigen, papillomavirus E7, myc, fos, and p53; which cell line upon culture at permissive temperatures results in functional protein expressed from said oncogene, thereby effecting the conditionally immortalizing phenotype, and upon shift of the cell line in culture to nonpermissive temperatures from permissive temperatures results in the absence of functional protein expressed from said oncogene thereby causing cessation of cell proliferation and at least the differentiated intestinal epithelial cell phenotype of expression of brush border enzymes sucrase isomaltase and aminopeptidase N and dipeptidyl peptidase IV, and of expression of keratin markers keratin 8 and keratin 21, and of expression of peripheral membrane protein ZO-1.

2. The intestinal epithelial cell line, according to claim 1, wherein the cell, prior to conditional immortalization, is selected from the group consisting of a stem cell, absorptive enterocyte, goblet cell, enteroendocrine cell, and crypt cell.

3. The intestinal epithelial cell line, according to claim 1, wherein said intestinal epithelial cell line has ben cultured at nonpermissive temperatures in the presence of extracellular matrix components enabling said intestinal epithelial cell line to be maintained at nonpermissive temperature for more than 18 days while exhibiting a tight epithelial morphology.

4. The intestinal epithelial cell line, according to claim 1, wherein said cell has been transfected with pZipSVtsa58.

* * * * *